United States Patent [19]
Cochran

[11] Patent Number: 4,561,856
[45] Date of Patent: Dec. 31, 1985

[54] INFUSION PUMP

[76] Inventor: Ulrich D. Cochran, 11525 Snapper Creek Dr. N., Miami, Fla. 33156

[21] Appl. No.: 524,338

[22] Filed: Aug. 18, 1983

[51] Int. Cl.$^4$ .............................................. A61M 5/00
[52] U.S. Cl. .................................. 604/143; 604/208; 604/211; 604/246
[58] Field of Search .............. 604/140, 141, 143, 131, 604/134, 135, 121, 118, 145, 246, 890, 208, 151, 207, 211; 122/DIG. 12; 222/306.46

[56] References Cited

U.S. PATENT DOCUMENTS

| | | | |
|---|---|---|---|
| 2,168,437 | 8/1939 | Buercklin | 604/143 |
| 2,545,017 | 3/1951 | Billingsley | 604/143 |
| 2,605,765 | 8/1952 | Kollsman | 604/135 |
| 3,433,223 | 3/1969 | Black | 604/143 |

*Primary Examiner*—Stephen C. Pellegrino
*Attorney, Agent, or Firm*—Henry W. Collins; Thomas R. Vigil

[57] ABSTRACT

The pump (10 or 150) is adapted to deliver liquid (24 or 166) to an individual. The pump comprises a syringe section (12 or 152) including a syringe barrel (18 or 160) having a nozzle (20 or 162) at one end and a syringe piston (22 or 170) in the barrel (18 or 160), an intermediate section (14 or 154 and 156) mounting a piston rod (46 or 265) for axial movement thereof, one end of the rod (46 or 265) being associated with the piston (22 or 170) for acting on the piston (22 or 170), and a drive section (16 or 158) at the other end of the pump (10 or 150) including a gas spring (113 or 300) associated with the other end of the piston rod (46 or 265) for acting on same to move the piston rod (46 or 265) which moves the syringe piston (22 or 170) to cause liquid to be delivered from the syringe barrel (18 or 160).

23 Claims, 4 Drawing Figures

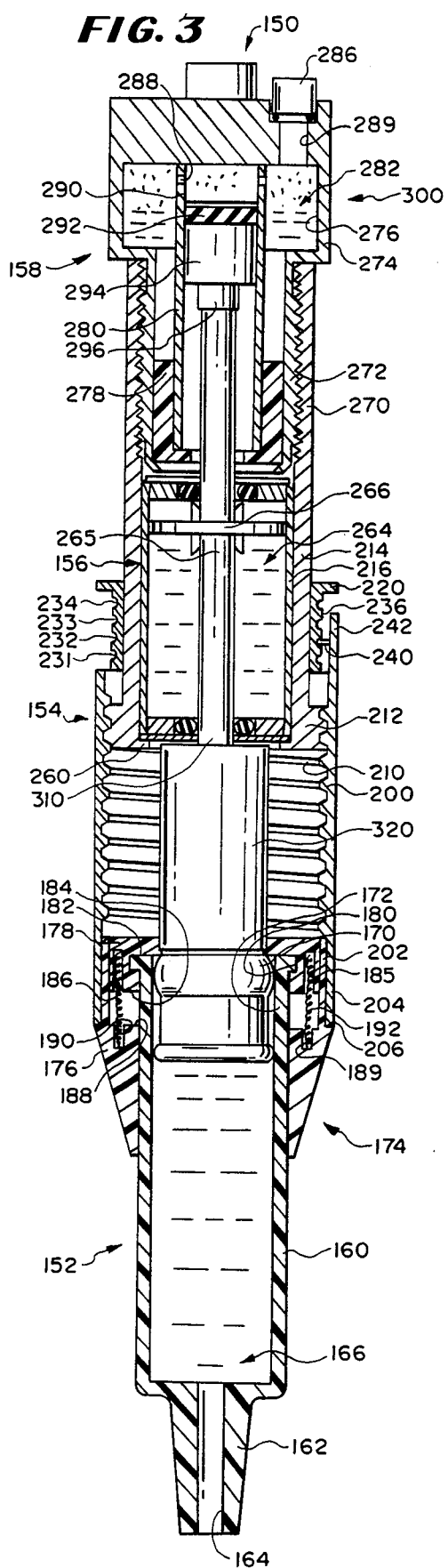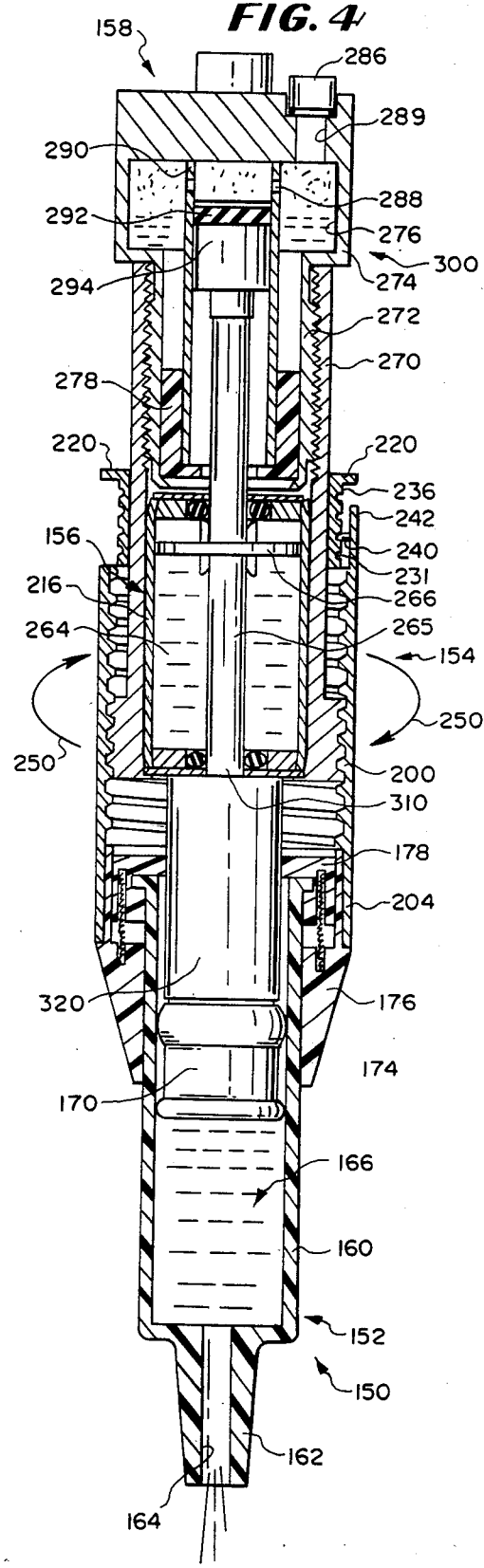

INFUSION PUMP

BACKGROUND OF THE INVENTION

1. Field of the Invention

The present invention relates to syringe type pumps having mechanisms therein or associated therewith for dispensing liquid at a very slow rate from the syringe barrel of the pump so as to meter the dispensing of liquid.

2. Description of the Prior Art

Heretofore various syringe devices and mechanisms associated therewith or incorporated therein for metering fluid from the syringe device have been proposed.

Examples of these previously proposed devices and mechanisms associated therewith are disclosed in the following U.S. Patents:

| U.S. PAT. NO. | PATENTEE |
| --- | --- |
| 2,474,496 | Rayman |
| 2,706,480 | Nensel |
| 2,875,761 | Helmer et al. |
| 3,325,061 | Ellsworth |
| 3,606,086 | Drummond et al. |
| 4,157,716 | Ruegg |
| 4,177,810 | Gourlandt |
| 4,190,048 | Sampson |
| 4,258,711 | Tucker et al. |
| 4,265,241 | Portner et al. |
| 4,274,558 | Clausen |

The Rayman U.S. Pat. No. 2,373,496 discloses a fluid injecting device having spaces between abutments or depressions on the plunger representing different units of volume of the contents within a syringe barrel of the device within which the plunger is received, which units are to be injected into a patient.

The Nensel U.S. Pat. No. 2,706,480 discloses an overdose preventing device mounted on a syringe in which a stop member is threadedly positioned within the syringe body to limit the maximum amount of fluid that can be drawn into the syringe body.

The Helmer et al. U.S. Pat. No. 2,875,761 discloses a multiple dosage syringe in which a dosage regulating device associated with the syringe has a pair of flexible legs engageable with recesses in the rear end portion of a plunger for enabling a user of the syringe to administer plural doses of equal volume.

The Ellsworth U.S. Pat. No. 3,325,061 discloses an hypodermic syringe having indicia on the syringe barrel and a slide member movable with a syringe plunger and having a forward end which indicates by its position relative to the indicia the amount of fluid dispensed from or withdrawn into the syringe barrel.

The Drummond et al. U.S. Pat. No. 3,606,086 discloses a microdispensing device wherein a series of recesses in a plunger holder are sequentially engageable by a spring detent so that a user may feel a click-like interengagement between the detent and the recesses as the plunger is moved into a syringe barrel whereby the user knows that a specified amount of fluid has been dispensed from or drawn into the syringe barrel. The plunger of the syringe works in conjunction with a capillary tube in effecting dispensing and withdrawing of liquid from or into the syringe barrel.

The Ruegg U.S. Pat. No. 4,157,716 discloses a motor driven liquid dose dispenser having two scaled rings movable relative to each other for indicating and limiting the quantity of liquid dispensed. One of the scale ring elements has a stop for limiting rotation thereof.

The Gourlandt U.S. Pat. No. 4,177,810 discloses a pneumatically operated automatic injection device for injecting liquids into animals.

The Sampson U.S. Pat. No. 4,190,048 discloses an infusate injection apparatus having a reservoir which is implanted in the human body and a pump which is also implanted in a human body. The pump is arranged so that it can be refilled as needed by simply injecting a fresh supply of infusate by means of a hypodermic needle through the patient's skin, through a pump septum and into the infusate chamber inside the apparatus. The act of refilling the pump can also serve to recharge a power supply or drive mechanism for the pump.

The Tucker et al. U.S. Pat. No. 4,258,711 discloses an implantable infusion apparatus having an infusate reservoir connected by way of a first flow path through a flow restricter to a mixing chamber and then into a vein. The reservoir and chamber volumes, the infusate concentration and chamber outlet flow rates are selected to provide an integrated dosage profile fitted to a patient. A restricter is provided and a drive capsule for the apparatus contains a compressible fluid such as a spring or two phase liquid for causing dispensing of liquid such as insulin into a patient's vein at a predetermined rate. The infusion apparatus is non-electrical.

The Portner et al. U.S. Pat. No. 4,265,241 discloses an implantable infusion device wherein a reservoir is defined by a bladder received in a chamber and the reservoir chamber can be pressurized by means of vapor pressure or a mechanical spring with a drug such as insulin under pressure in the reservoir being released in response to an externally applied electrical signal via a solenoid.

The Clausen U.S. Pat. No. 4,274,558 discloses a device for dispensing a liquid by use of a peristaltic type pump acting on a tubing.

As will be described in greater detail hereinafter, the pump of the present invention differs from the previously proposed dispensing, metering and pumping devices by providing a simple piston and cylinder type pump wherein the piston rod of the pump is driven by a gas spring.

Further, a dampening or timing mechanism is associated with the piston rod for dampening axial movement thereof whereby liquid is dispensed or metered from a syringe barrel at a predetermined rate to provide a desired basal dispensing or metering of liquids such as insulin, heparin or the like.

Still further, the pump of the present invention can be provided with a bolus control mechanism for providing a bolus infusion of a liquid, such as a drug or insulin, when such is needed, such bolus control mechanism being adapted to override a basal delivery system of the pump and yet permit the basal delivery system to continue to function after a bolus infusion.

SUMMARY OF THE INVENTION

According to the invention there is provided a pump for delivering liquid to an individual in either an automatic basal mode of delivery or a manual bolus mode of delivery, said pump comprising a syringe section including a syringe barrel having a nozzle at one end and a syringe piston in said barrel, an intermediate section mounting a piston rod for axial movement thereof, one end of said rod being associated with said piston for acting on said piston, said intermediate section including timing means for causing delivery of liquid at a constant rate of basal delivery, a drive section at the other end of said pump including a gas spring associated with the other end of said piston rod for acting on same to move said piston rod to move said syringe piston to cause liquid to be delivered from said syringe barrel and a bolus control mechanism associated with said drive section for causing a bolus delivery of liquid, overriding the basal mode of delivery.

The pump provides a basal delivery and the bolus control mechanism is adapted to override the basal delivery and yet permit the basal delivery function of the pump to continue after a bolus infusion. Such bolus control mechanism includes a bolus control sleeve which is fixed at one end to the syringe barrel and is rotatable on a housing member fixed to the drive section so as to cause relative movement between the syringe piston and the syringe barrel.

Additionally, a collar spring mechanism is situated between the control sleeve and the syringe barrel and has a compressible spring which can be compressed when there is attempted relative movement between the syringe piston and the syringe barrel thereby to provide compensation for the back pressure of the fluid on the syringe piston which limits the speed at which the syringe piston can move relative to the syringe barrel, the spring compression then effecting the bolus movement of the syringe piston in the syringe barrel but at a slowed down rate of movement due to the back pressure.

BRIEF DESCRIPTION OF THE DRAWINGS

FIG. 3 is an elevational sectional view of an embodiment of an insulin infusion pump constructed according to the teachings of the present invention for providing a bolus as well as a basal dispensing of insulin from the pump.

FIG. 4 is an elevational sectional view of the pump shown in FIG. 3 and is similar to the view shown in FIG. 3, but with a bolus infusion control sleeve axially displaced relative to a dampening cylinder as a result of several bolus dispensings of insulin from the pump and shows a spring assembly compressed just after a bolus movement of the bolus control sleeve.

DESCRIPTION OF THE PREFERRED EMBODIMENT

Figure 1:
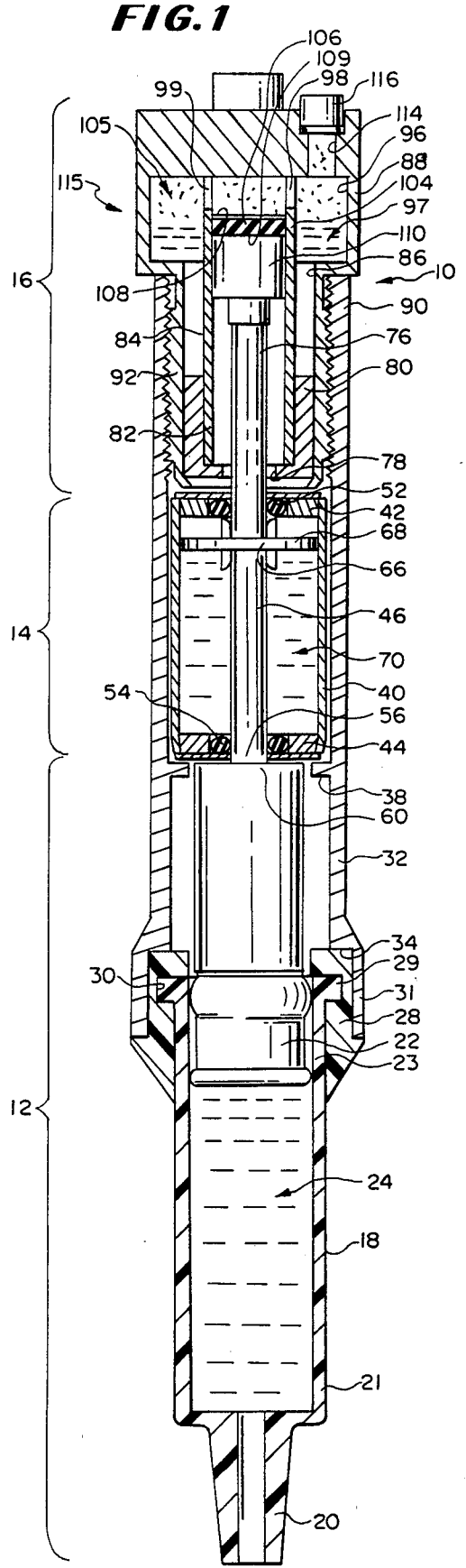
FIG. 1 is an elevational sectional view of an infusion pump constructed according to the teachings of the present invention for a basal dispensing of a drug or fluid therefrom.

Referring now to FIG. 1, there is illustrated therein an infusion pump which is generally identified by reference numeral 10. The infusion pump 10 includes a lower syringe section 12, an intermediate dampening section 14 and an upper drive section 16.

The syringe section 12 includes a syringe barrel 18 having a nozzle 20 at the lower end 21 thereof and a syringe piston 22 received in the upper end 23 thereof. A solution 24 having a predetermined concentration of a substance such as insulin, a drug, or a nutrient therein is drawn into the barrel 18 for being dispensed from the pump as described in greater detail below.

The nozzle 20 is sized to receive a catheter (not shown).

It will be understood that the other end of the catheter (not shown) can be connected to a needle which is inserted into an individual's muscle tissue or bloodstream for supplying the solution 24 to the individual.

Coupled to the upper end 23 of the syringe barrel 18 is a collar member 28 in which barrel 18 is inserted and rotated to place bayonet flanges 29 into mating slots 30 in collar member 28. Then, fixed to and seated on the collar member 28 is one end 31 of a cylindrical housing 32 which extends through the intermediate section 14 to the drive section 16. The cylindrical housing 32 is made of metal and has a shoulder 34 at a lower end 31 thereof for resting on the collar member 28. Then, at a predetermined distance above the shoulder 34, there is formed on the cylindrical housing 32 an inwardly extending annular flange 38. Seated on and above this flange 38 is a cylindrical barrel 40 having an upper end 42 and a lower end 44, through which ends 42 and 44 is received a piston rod 46. As shown, O rings 52 and 54 are mounted in the ends 42 and 44 for sealingly engaging the piston rod 46.

The piston rod 46 has a lower end 56 which acts upon or pushes an upper end 60 of the syringe piston 22.

Within the cylindrical barrel 40 is situated a disc 66 that is fixed on the piston rod 46 and which, either has an outer diameter less than the inner diameter of the cylindrical barrel 40 or has port openings 68 therethrough for permitting flow of a dampening or dilatant liquid 70 around or through the disc 66.

The dilatant liquid 70 serves to control and time downward movement of the piston rod 46. For this reason, the intermediate section 14 can be referred to as a timing section 14 for timing downward movement of the piston rod 46.

An upper end 76 of the piston rod 46 extends through an opening 78 in the bottom end of a cup-shaped plug 80 having a lower end 82 of a cylinder 84 received therein and extending upwardly therefrom into a chamber 86 within a housing 88 in the drive section 16 of the pump 10. Here it will be seen that an upper end 90 of the cylindrical housing 32 is threadedly received about and around a lower end 92 of the drive section housing 88.

The cylinder 84 has the lower end 82 received in the cup-shaped plug 80 and extends to the top of the chamber 86 within the housing 88. As shown, the top of chamber 86 has a larger in diameter portion 96 in which is received a liquid/gas fluid 97 such as monodichlorodifluoro methane sold under the trademark FREON. Other low boiling-point liquids also may be used such as FREON 22 TM, FREON 12 TM, FREON 115 TM, butane or methyl chloride. Also port openings 98 and 99 are formed in top end 104 of the cylinder 84 so that the gas 105 from the liquid/gas fluid 97 in the chamber 86 can flow into the top of the cylinder 84 for acting on a piston 106 made of an elastomeric material that forms a movable seal within the cylinder 84. Gas 105 from the liquid/gas fluid 97 in the chamber 86 acting upon upper surface 108 of piston 106 urges the lower surface 109 of the piston 106 against a gas spring follower 110 which in turn abuts and acts upon, and is preferably connected to, the upper end 76 of the piston rod 46.

As shown, drive section housing 88 has a port 114 communicating the exterior environment with the chamber 86 whereby, after the chamber 86 has been filled with a gas/liquid fluid such as freon, the port opening 114 can be sealed by a screw-threaded plug 116.

The chamber 86, 96 with the gas/liquid fluid 97 therein defines a gas spring 115 which exerts the vapor pressure of the gas 105 against the piston 106 and provides a constant force on the follower 110 acting on the upper end 76 of the piston rod 46.

The high viscosity dampening fluid 70 flows through the clearance area between the outer periphery of the disc 66 and the inner surface of the barrel 40 at a constant rate which provides for timing of a basal cycle of dispensing of the solution 24 out the nozzle 20 and into a catheter (not shown). In this way, the syringe plunger or piston 22 gradually expels insulin solution 24 from the syringe barrel 18.

FREON 115 TM is an ideal gas/liquid fluid for use in the chamber 86, 96. In this respect, the FREON 115 TM vaporizes to a gas at a pressure of approximately 180 psi and a temperature of approximately 93° F. As the piston 106 is moved downwardly by the gas pressure acting on the upper surface 108 thereof, more liquid will vaporize into gas and the pressure of the gas will be constant so that there is a constant force applied by the gas spring 115 to the piston 106.

The basal delivery extends over a 24-hour period and the syringe barrel 18 can be provided with a 12-hour reserve of solution 24 therein.

It is contemplated that the infusion pump 10 will be positioned adjacent the individual's body so as to have a temperature close to the skin temperature of the individual, which is typically 93.5°. In this way, the temperature of the infusion pump 10 will be within the ideal operating temperature range for the gas spring 113 which is 92° F.±5° F.

The rate is defined by the high viscosity dilatant liquid 70 and the space between the outer diameter of the disc 66 and the inner diameter of the barrel 40 and can be chosen to provide a continuous infusion of insulin solution into a patient of 20 microliters per hour plus or minus 5% at 91° F. This provides for a delivery or infusion of 480 microliters of insulin solution over a period of 24 hours. Also, the volume of the syringe barrel 18 with the syringe piston or plunger 22 in its uppermost position is approximately 1,600 microliters thereby providing a 240 microliter basal reserve capacity of insulin solution for delivery over a 12-hour period.

The syringe dedication for syringe barrel 18 is:

| | |
|---|---|
| Basal delivery (for 24 hours) | 480 μl |
| Basal reserve (for 12 hours) | 240 μl |
| Purging of catheter | 100 μl |
| | 820 μl |

Also, 780 μl can be provided for bolus delivery as will be described in further detail in connection with the description of FIGS. 3 and 4, thereby to provide a total capacity of 1,600 μl.

Figure 2:
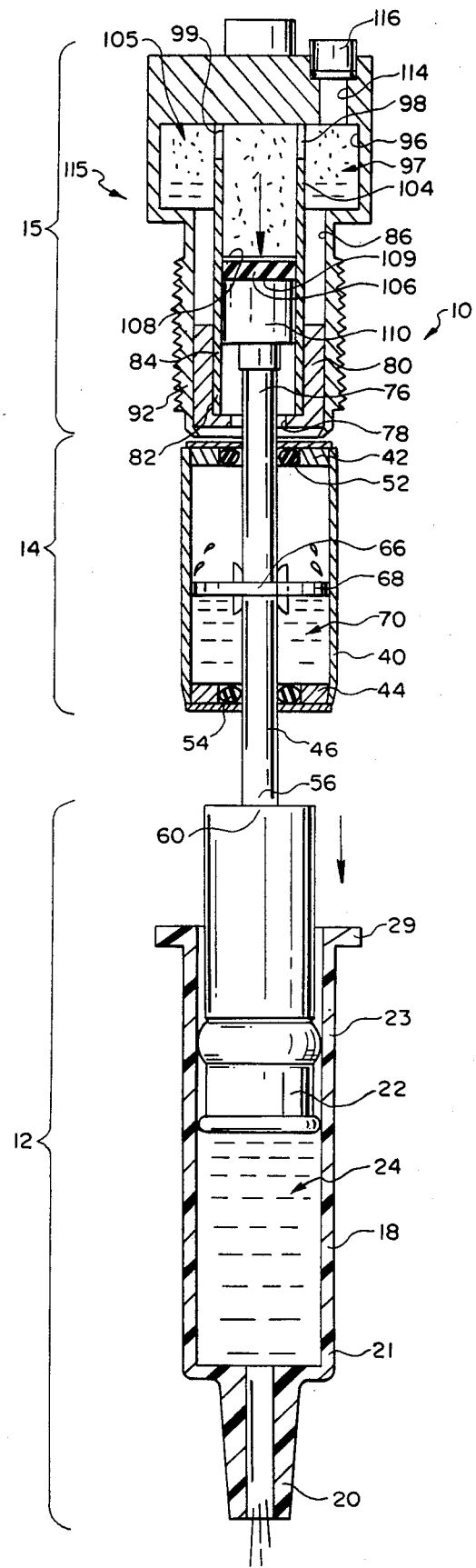
FIG. 2 is an elevational sectional view of the pump shown in FIG. 1 and is similar to the view shown in FIG. 1, but with the outer casing of the pump not shown and with the syringe piston of the pump displaced downwardly under the action of a gas spring at the upper end of the pump.

The manner in which the infusion pump 10 operates is illustrated in FIG. 2 where a quantity of solution 24 has been dispensed through the nozzle 20 as a result of the action of the vapor pressure of the gas 105 in the upper end 104 of the cylinder 84 on piston 100. The force of the vapor pressure of the gas 105 is indicated by an arrow 120 in FIG. 2.

Referring now to FIG. 3, there is illustrated therein another embodiment of the infusion pump of the present invention which is generally identified by reference numeral 150. In this embodiment, there is provided a lower syringe section 152, a first intermediate bolus control section 154, a second intermediate dampening or timing section 156 and an upper drive section 158. As with the infusion pump 10 shown in FIGS. 1 and 2, the infusion pump 150 shown in FIG. 3 has in the syringe section 152 thereof, a syringe barrel 160 having a nozzle 162 at the lower end thereof with a metering orifice 164 in the nozzle 162. Quantitive metering is controlled by the internal diameter of the syringe and by the speed of movement of a piston rod 256 under the force of a gas spring 300 through the dampening section 156 as will be described in greater detail below. A quantity of solution 166 is received within the syringe barrel 160.

A syringe piston or plunger 170 is received in an upper end 172 of the syringe barrel 160. As shown, a spring collar assembly 174 is fixed to the upper end 172 of the syringe barrel 160 and includes a first or lower generally conical-shaped collar portion 176 slidably received on the syringe barrel 160 and a second or upper collar portion 178 having a groove 180 therein in which is received an outwardly extending flange 182 at the upper end 172 of the syringe barrel 160. Then, in upwardly facing side 184 of collar portion 176 there are formed at least two bores 185 and 186 and in opposed downwardly facing side 188 of collar portion 178 there are formed at least two aligned bores 189 and 190.

Within each pair of aligned bores 185, 189 and 186, 190, there is received a spring 192, each of which is connected at its bottom end to collar portion 176 and at its upper end to collar portion 178.

As will be described in greater detail hereinafter, when a bolus control sleeve 200 in the bolus control section 154 is rotated to cause axial movement of the sleeve 200 and the lower collar portion 176 relative to the syringe piston 170 to make a bolus delivery or infusion of solution, initially, the upper collar portion 178 does not move due to back pressure generated by the small lumen of the catheter connected to nozzle 162 and lower collar portion 176 slides upwardly on syringe barrel 160 compressing springs 192 between collar portions 176 and 178 as shown in FIG. 4. The springs 192 will then urge the syringe barrel 160 upwardly relative to the piston 170 until the bolus delivery has been completed and the springs 192 are relaxed.

As shown, the lower collar portion 176 has an upwardly extending sleeve portion 202 about which is received and to which is fixed lower end 204 of the bolus control sleeve 200. Here, the lower end 204 of the bolus sleeve 200 rests on a shoulder 206 on the lower collar portion 176 adjacent sleeve portion 202. The bolus control sleeve 204 has internal threads 210 and such threads 210 are received over a threaded lower end 212 of an intermediate housing member 214 mounting a cylindrical barrel or capsule 216.

Associated with an upper end 218 of the bolus control sleeve 200 and movable therewith is a bolus calibration ring or sleeve 220 received on and slidable on the housing ring 214. The calibration ring 220 has one or more axially spaced annular grooves therein and, in FIGS. 3 and 4, four such grooves 231–234 are shown on an outer surface 236 of the ring 220. Each of the grooves 231–234 has a predetermined number of depressions in the bottom thereof which are equally spaced in the grooves 231–234 about the ring 220.

Each of the grooves 231-234 in the bolus calibration ring 220 provides a tracking path for a detent pin 240 mounted to and extending from a tab 242 extending upwardly from the bolus control sleeve 200. If desired, the tab 242 can have a hole therein through which the pin 240 can extend. Then the pin 240 can be mounted to a leaf spring which is fixed to the outer surface of control sleeve 200.

On the other hand, as shown, the bolus control sleeve 200 can be made of metal or plastic which can flex or spring so that the cantilevered tab 242 can flex inwardly and outwardly of the position thereof shown in FIGS. 3 and 4 so that each time the sleeve 200 is rotated so as to move the pin 240 out of a depression at the bottom of annular groove 232, the cantilevered tab 242 can flex outwardly until the pin 240 mates with the next depression in the groove 232.

This will cause a tactile and audible click and this click sound or feel indicates to a user of the pump 150 that one unit, e.g., an international unit of insulin, of the diluted solution 166 in the spring barrel 160, has been metered from the syringe barrel 160, as a result of the partial rotation of the bolus control sleeve 200 around the axis of the pump 150 as indicated by the arrows 250 in FIG. 4.

For the purpose of a simple example of use of the pump 150 in the bolus delivery mode, pump 150 will be considered as delivering an insulin solution.

In the illustrated embodiment, four bolus calibration grooves 231-234 are provided in the bolus calibraring 220. Each groove 231-234 will have a different number of equally spaced depressions therein which will cause that number of tactile "click" points during 360° rotation of the bolus control sleeve 200. The number of depressions in each groove 231-234 is related to and calibrated for different insulin concentrations in the insulin solution 166 to provide one click for each quantum of insulin delivered as determined by the pitch of threads 210, the axial travel of sleeve 200 caused by a 360° rotation of the control sleeve threads 210 about end 212 of housing 214 and the inner diameter of syringe barrel 160.

The bolus calibration ring 220 is axially movable but not rotatable on the housing 214 and may have a spline connection with housing 214 to permit such axial movement but not rotatable movement thereof.

Typically, one groove 231 is provided for a six insulin unit delivery upon 360° rotation of sleeve 220 and with six equally spaced depressions in groove 231, the groove 231 is divided into six equal spaces between the depressions in the groove 231 so that each click represents one unit delivered. This means that the axial length of movement of the housing 214 into sleeve 200 for one revolution of sleeve 200 times the cross sectional area within syringe barrel 160 is a given volume and for the dilution of the insulin solution 166 in the syringe barrel 160, the given volume contains six insulin units.

For a seven unit delivery, another groove, e.g., groove 232, can have seven spaces between depressions and for a five unit delivery, a further groove 233 can have five spaces between the detent forming depressions. By engaging the pin 240 in the appropriate groove 231-234 for the dilution of insulin in the syringe barrel 160, the patient is always delivering one unit per click.

It will be understood that the choice of calibration groove 231-234 utilized for a particular individual will depend upon the concentration of insulin in the insulin solution 166 that is drawn into the syringe barrel 160.

Further it will be understood that the pitch of the screw threads 210 is in such a ratio to the internal diameter (volume) of the syringe barrel 160 as to give a desired displacement, e.g., 100 microliters, per revolution of the bolus control sleeve 200.

The basal delivery system of the infusion pump 150 shown in FIGS. 3 and 4 is substantially identical to the basal delivery system of the pump 10 shown in FIGS. 1 and 2 and includes an inwardly extending flange 260 at the lower end 212 of the intermediate housing 214 for holding dampening or timing barrel or capsule 216 and having a high viscosity dampening fluid 264 therein. A piston rod 265 extends through the timing capsule 216 and has a disc 266 mounted thereon around which dampening fluid 264 will flow as the piston rod 265 is urged downwardly or upwardly.

Upper end 270 of the intermediate housing 214 is threaded on the inner cylindrical surface thereof and received over threaded lower end 272 of a drive section housing 272 having a chamber 276 therein, a cup-shaped plug 278 therein and a cylinder 280 therein. A liquid/gas fluid 282 is inserted in the chamber 276 through a port 284 which is then capped by a screwthreaded plug 286. The gas in the upper end of the chamber 276 will flow through port openings 288 in upper end 290 of the cylinder 280 and act upon a piston or gas seal member 292 which is typically made of an elastomeric material. This piston 292 acts on a gas spring follower 294 which coacts with or is connected to upper end 296 of the piston rod 265. The chamber 276 and the saturated gas/liquid fluid 282, such as FREON 115 TM, therein, form a gas spring 300 which forms part of basal delivery system of the insulin infusion pump 15.

It will be appreciated that the cylindrical barrel or capsule 40 of the pump 10 or 216 of the pump 150 can be considered a dampening or timing capsule 40 or 216 since the space between the disc 66 or 266 and the inner surface of the barrel 40 or 216, and the viscosity of the high viscosity fluid 70 or 264 determine how long it will take to move the disc 66 or 266 from one end of the barrel 40 or 216 to the other end of the barrel 40 or 216 when it is acted upon by a constant gas spring force acting on the piston rod 46 or 265. In this respect, by means of varying the clearance between the disc 66 or 266 and the inner surface of the barrel 40 or 216 and/or by varying the thrust of the gas spring 115 or 300 by changing the type of gas/liquid fluid 47 or 282 utilized, or by changing the upper surface area of the piston 106 or 292 on which the gas acts, any desired rate of advance of the piston rod 46 or 265 can be achieved.

In the pump 10 shown in FIGS. 1 and 2, the syringe barrel 18 is fixed to the lower end 30 of the housing 32 in which the cylindrical barrel or capsule 40 is mounted for providing a timing function.

In the pump 150 shown in FIGS. 3 and 4, the pitch of the threads 210 in the bolus control sleeve 200 preferably is such as to provide a displacement of 100 microliters of insulin solution upon one complete revolution (360° of rotation) of the screw threads 210 on the lower end 212 of the intermediate housing 214.

Also it is to be appreciated that the depressions in the grooves 231-234 can be spaced so as to provide a calibration in microliters or any other desired unit of measurement.

This is accomplished by the pitch selected for the screw threads 210, the inner diameter of syringe barrel 160, and the number of interruptions or depressions provided in a particular groove 231-234 on the calibration ring 220.

To start delivery of a fresh supply of drug or insulin, the pump 150 is uncoupled from a delivery catheter. Next, the drive section housing 274 is unthreaded from the intermediate housing 214 to disengage the gas spring 300 from the pump 150.

The pump 150 is loaded first by unscrewing the gas spring 300 from the upper end 270 of housing 214 and removing the timing capsule 216. If the timing capsule 216 is fully traversed, it is reversed so the exposed end of rod 265 protrudes upward and the capsule 216 is reinserted in drive housing 214.

Alternatively, a second capsule 216 which has been traversed by a spring pressure device may be substituted.

The gas spring 300 is then screwed back into the housing 214 to its working position with the gas spring piston 292 being depressed by the protruding end of the rod 265.

It will be noted that in this particular embodiment of the pump 150 described, upper and lower ends 296 and 310 of the piston rod 265 are not fixed to the respective pistons 294 and 170. More specifically, the lower end 210 is not fixed to cylindrical member 320 forming part of and associated with piston 170 of the syringe section 152.

It is to be noted that if the barrel or capsule 220 with piston rod 265 therein is changed after 24 hours, the piston rod 265 will not be fully extended. For this purpose, a separate housing or container is provided for carrying one or more gas springs 300 and one or more syringe barrels 160 and one or more timing capsules 216 with piston rod 265 therein. Then spring loading devices are provided in the container for mounting on the alternate timing capsules 216 to move piston rods 265 thereof which have not been fully extended in use to a fully extended position of each piston rod 265.

After a timing capsule 216 has been inserted into housing 214, the gas spring 300 has been screwed into its operating position and the bolus control sleeve 200 has been fully extended to its "start" position, a fresh syringe barrel 160 is fitted onto the lower end 204 at the bolus control sleeve 200, and is then back filled until syringe piston 170, 320 contacts timing capsule piston rod 265.

Then it may be desirable to rotate the bolus control sleeve 200 to expel any air that might be in the orifice 164 of the nozzle 162 or in a catheter extending therefrom.

Now the pump is ready to be connected to a delivery catheter to resume basal dispensing of insulin solution to an individual. It may be desirable to prefill the catheter via rotation of the bolus control sleeve 200.

It will be understood that after the individual has undergone some activity, such as eating a meal, where his need for insulin will be increased, he or she will know that the bolus control sleeve should be rotated one or more clicks to supply one international unit of insulin.

In one realization of the pump 150 of the present invention, the length of the pump 150 was approximately 4 inches with an outer diameter of approximately ⅜ inch. The pump 150 weighed 30 grams when empty and 31.6 grams when fully charged with a quantity of insulin solution 166.

The metal and plastic parts of the pump were made of non-allergenic materials and materials which are not reactive with human skin.

The experimental model or realization of the pump 150 was constructed to provide a basal dispensing or infusion of an insulin solution at the rate of 20 microliters per hour plus or minus 5% at 91° F. This provided for an infusion of 480 microliters over a period of 24 hours. The syringe barrel 160 had a capacity for 240 more microliters so as to provide a basal reserve capacity of 240 microliters. The total capacity or volume of the syringe barrel 160 was 1600 microliters thereby providing a 240 microliter basal reserve capacity of insulin solution for delivery over a 12 hour period.

The syringe dedication for syringe barrel 160 is as follows:

| | |
|---|---|
| basal delivery (for 24 hours) | 480 μl |
| basal reserve (for 24 hours) | 240 μl |
| purging of catheter | 100 μl |
| | 820 μl |
| available for bolus delivery as needed | 780 μl |
| | 1600 μl |

Metering is accomplished as follows. The gas spring 300 exerts a force against timing capsule piston rod 265, dilatant compound 264 in capsule 216 is forced from the lower chamber beneath disc 266 to the upper chamber above disc 260 through the space or clearance between disc 266 and capsule 216 and/or through bypass orifices in the disc 266 thereby allowing the rod 265 and disc 266 to progress axially downwardly viewing same as shown in the drawings, forcing syringe piston 170 toward orifice 164.

The factors determining metering (μl/hr.) are:
A. Gas spring force
B. Timing rate of capsule under gas spring force
C. Cross sectional area of syring barrel 160.

The bolus delivery was accomplished by rotating the control sleeve 200 and each click constituted one quantum of insulin, such as one I.U., with the solution having the right dilution of insulin to be properly correlated with the volume displacement per fractional turn of sleeve 200.

The force of the gas spring 300 was such that a spring loading torque was provided that would not exceed the capability of an eight year old child.

The experimental model or realization of the pump 150 was designed to operate at a temperature of 91° F. and at a normal ambient operating pressure between atmospheric pressure and the pressure that would exist at an altitude of 5000 feet.

It is to be appreciated that the pump 10 or 150 of the present invention can be used for other purposes besides dispensing or infusing insulin.

From the foregoing description it will be apparent that many modifications can be made to the pump 10 or 150 without departing from the teachings of the invention. Also, it will be appreciated that the pump 10 or 150 of the present invention has a number of advantages some of which have been described above and others of which are inherent in the invention. Accordingly, the scope of the invention is only to be limited as necessitated by the accompanying claims.

I claim:

1. A pump for delivering liquid to an individual in either an automatic basal mode of delivery or a manual bolus mode of delivery, said pump comprising a syringe section including a syringe barrel having a nozzle at one end and a syringe piston in said barrel, an intermediate section mounting a piston rod for axial movement thereof, one end of said rod being associated with said piston for acting on said piston, said intermediate section including timing means for causing delivery of liquid at a contant rate of basal delivery, a drive section at the other end of said pump including a gas spring associated with the other end of said piston rod for acting on same to move said piston rod to move said syringe piston to cause liquid to be delivered from said syringe barrel and bolus control means associated with said drive section for causing a bolus delivery of liquid, overriding the basal mode of delivery.

2. The pump of claim 1 wherein said drive section comprises a housing having a chamber therein, a liquid/gas fluid in said chamber, a cylinder, a drive piston in said cylinder and associated with said other end of said piston rod, and means communicating said chamber with one end of said cylinder to permit vapor pressure of gas from said chamber to act on said drive piston which in turn acts on said piston rod to cause said rod to act on said syringe piston.

3. The pump of claim 2 wherein said liquid/gas fluid is a low boiling point fluid having a high vapor pressure at ambient temperatures.

4. The pump of claim 1 including means in said intermediate section for timing the movement of said piston rod.

5. The pump of claim 1 wherein said timing means comprise a capsule through which said piston rod extends, said piston rod having a disc mounted thereon intermediate the ends thereof within said capsule, said capsule being filled with a high dilatant material, and said disc having passage means therethrough or thereabout by which the dilatant material can flow from one side of said disc to the other side of said disc when said gas spring is acting on one end of said piston rod.

6. The pump of claim 5 wherein said passage means comprise a clearance between the outer periphery of said disc and an inner wall of said capsule.

7. The pump of claim 1 wherein said drive section includes a drive section housing and said gas spring is defined by a chamber in said housing with said gas/liquid fluid being situated in said chamber.

8. The pump of claim 7 wherein said intermediate section includes an intermediate housing which is releasably fixed to one end of said drive section housing and to one end of said syringe barrel.

9. The pump of claim 8 including a timing capsule received within said intermediate housing, said capsule having a dilatant fluid therein, and a portion of said piston rod being received in said capsule, said dilatant fluid acting on said portion of said piston rod to dampen movement of said piston rod, said dampening action serving to time the movement of said piston rod as a constant force is exerted by said gas spring on said piston rod thereby to meter liquid from said syringe barrel at a constant rate.

10. The pump of claim 1 comprising bolus control means in the form of a sleeve having one end mounted to one end of said syringe barrel and another end connected to said drive section and axially movable relative to said drive section whereby predetermined increments of axial movement of said bolus control means in the form of a sleeve relative to said drive section causes relative movement between said syringe piston and said syringe barrel to deliver from said syringe barrel a predetermined quantity of liquid.

11. The pump of claim 10 wherein said bolus control sleeve is mounted to said one end of said syringe barrel by a collar spring assembly which, upon axial movement of said control sleeve relative to said drive section to cause said syringe piston to push liquid out of said syringe barrel, will compress spring means in said collar spring assembly to compensate for back pressure of the liquid acting on said syringe piston with the compressed spring force eventually overcoming the back pressure.

12. The pump of claim 10 wherein said piston rod and/or said syringe piston extend into said bolus control sleeve for coaction with each other and said bolus control sleeve is threadedly received on a housing member depending from or forming part of said drive section, so that rotation of said bolus control sleeve on said housing member will cause relative axial movement of said bolus control sleeve and said syringe barrel relative to said syringe piston thereby to cause a bolus amount of liquid to be ejected from said syringe barrel.

13. The pump of claim 12 wherein the pitch of threads on the inner surface of said bolus control sleeve are chosen so that one complete revolution of said control sleeve will cause a predetermined relative axial movement between said syringe piston and said syringe barrel such that the volume contained within this axial movement is equivalent to a given quantum of liquid.

14. The pump of claim 13 including a bolus calibration ring slidably received but not rotatable on said housing member and having at least one annular groove therein, the other end of said bolus control sleeve having at least a portion thereof extending outside of and adjacent to said bolus calibration ring, said control sleeve having a pin extending inwardly therefrom for engagement in said groove, and said groove having a predetermined number of equally spaced depressions in the bottom thereof into which said pin can be received such that rotation of said bolus control sleeve relative to said bolus calibration ring will cause said pin to move in said slot from one depression to an adjacent depression and cause a "click" type sound when the pin falls into the adjacent depression thereby to indicate to an operator of the pump that the control sleeve has been rotated a predetermined distance to cause a predetermined bolus delivery of liquid from said syringe barrel.

15. The pump of claim 14 wherein said calibration control sleeve is axially movable but not rotatable on said housing member and has a plurality of annular grooves therein each one having a different number of depressions therein for different calibrations correlated to different concentrations of a substance, such as a drug, in the liquid in the syringe barrel.

16. An insulin infusion pump comprising means for storing a supply of insulin solution and including outlet means, drive means associated with said storage means for acting on said storage means to cause dispensing of liquid therefrom at a predetermined slow rate, and timing means associated with said drive means for dampening movement of a drive member of said drive means, said timing means including a capsule having a dilatant material therein, said drive means including a piston rod extending through said capsule, and means on said piston rod within said capsule against which the dilatant material acts for causing said piston rod to move at a timed rate.

17. The pump of claim 10 wherein said bolus control sleeve has a spring biased movable connection between one end of said control sleeve and one end of said syringe barrel whereby upon axial movement of said control sleeve causing movement of said piston against the liquid in said syringe barrel, spring means of said connection are initially compressed to absorb back pressure acting on the syringe piston as a result of constrains in the flow of liquid from the syringe barrel such as caused by a small lumen in a tubing of a delivery system coupled to a nozzle of said syringe barrel.

18. The pump of claim 17 wherein said connecting means include a first collar portion fixed to an end of said bolus control sleeve and slidably received on said syringe barrel, a second collar portion fixed to an end of said syringe barrel and slidable relative to said first collar portion and spring means coupled to and between said collar portions and being compressible upon axial displacement of said bolus control sleeve in one direction.

19. The pump of claim 18 wherein said drive means comprise a housing having a chamber therein and means for communicating one end of said chamber to a cylinder in which is located a piston which coacts with one end of said drive member and a gas/liquid fluid in said chamber for forming a gas spring which acts upon said piston coacting with one end of said drive member.

20. The pump of claim 18 wherein said means for causing said piston rod to move at a timed rate include a disc which is fixed on said piston rod and which is movable within said capsule against the dilatant material, said disc having means for permitting fluid flow from one side of said disc to the other side of said disc, the space or dimensions of said fluid flow passage means defining the timing function of said timing means.

21. The pump of claim 18 including a bolus dispensing means operable to override said timing means to cause an accurately measured bolus infusion of insulin from said outlet means.

22. The pump of claim 21 wherein said means for storing a supply of insulin solution includes a syringe barrel having a syringe piston therein and wherein said drive means are operable to act on said syringe piston, and wherein said bolus control means includes means for causing relative axial movement between said syringe piston and said syringe barrel thereby to cause an accurately measured bolus delivery of insulin solution from said syringe barrel.

23. The pump of claim 22 wherein said bolus control means includes back pressure relief means which are operable upon a force being generated by said bolus control means to cause relative axial movement between said syringe piston and said syringe barrel to absorb such force due to back pressure of insulin solution acting on said piston and slowly apply said force to said insulin solution in said syringe barrel to cause the desired bolus amount of insulin solution to be dispensed from the syringe barrel as fast as the dimensions of a fluid delivery system coupled to a syringe barrel permit.

* * * * *